(12) United States Patent
Lechot

(10) Patent No.: US 7,988,692 B2
(45) Date of Patent: Aug. 2, 2011

(54) SURGICAL TOOL HOLDER AND SURGICAL TOOL

(75) Inventor: André Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 888 days.

(21) Appl. No.: 11/962,562

(22) Filed: Dec. 21, 2007

(65) Prior Publication Data
US 2008/0177265 A1    Jul. 24, 2008

Related U.S. Application Data

(60) Provisional application No. 60/882,247, filed on Dec. 28, 2006, provisional application No. 60/871,406, filed on Dec. 21, 2006.

(51) Int. Cl.
*A61B 17/00* (2006.01)
*A61B 17/32* (2006.01)
(52) U.S. Cl. .......................................................... 606/79
(58) Field of Classification Search ................ 606/79, 606/80, 81–85
See application file for complete search history.

(56) References Cited

U.S. PATENT DOCUMENTS

| | | | | |
|---|---|---|---|---|
| 5,236,433 A | * | 8/1993 | Salyer | 606/91 |
| 5,295,992 A | | 3/1994 | Cameron | |
| 5,658,290 A | * | 8/1997 | Lechot | 606/80 |
| 6,250,858 B1 | * | 6/2001 | Salyer | 408/239 R |
| 6,264,647 B1 | | 7/2001 | Lechot | |
| 7,048,740 B2 | * | 5/2006 | White et al. | 606/80 |
| 7,296,804 B2 | * | 11/2007 | Lechot et al. | 279/75 |
| 7,326,198 B2 | * | 2/2008 | Desarzens et al. | 606/1 |

(Continued)

FOREIGN PATENT DOCUMENTS
CN    1672643    9/2005
(Continued)

OTHER PUBLICATIONS
Office Action from European Patent Office dated Apr. 8, 2011.
(Continued)

*Primary Examiner* — Thomas C. Barrett
*Assistant Examiner* — Christopher Beccia
(74) *Attorney, Agent, or Firm* — Michael F. Scalise

(57) ABSTRACT

A surgical tool holder 12 and tool system 10 is provided. The surgical tool holder (12) is adapted to connect to a tool support (14) having an interface receiver (36). The tool support provides a mount for a surgical tool head. The tool holder (12) includes a center rod (20), a tool interface (28) and a quick connect mechanism (50). The center rod (20) has a first shank end (24) and a second tool end (26). The tool interface (28) is disposed on the tool end (26) of the center rod (20). The tool interface (28) has at least one transversely extending portion (44, 44*a*), extending radially outward, beyond the diameter of the center rod (20) at the tool end (26). The interface (28) is adapted to engage with the interface receiver (36). The quick connect mechanism (50) is disposed on the center rod (20) to move in a rotationally-constrained manner thereon proximate the tool interface (28). The mechanism (50) includes protrusions (66) biased to bear against and engage the tool support (14) when the tool support is engaged with the tool interface (28). This securely holds the tool support (14) and prevents its relative rotation with respect to the tool holder (12).

25 Claims, 15 Drawing Sheets

U.S. PATENT DOCUMENTS 7,850,692 B2 * 12/2010 White et al. .................. 606/81
7,850,693 B2 * 12/2010 Wolford ........................ 606/81

FOREIGN PATENT DOCUMENTS

| EP | 0704191 | 3/1996 |
|----|---------|--------|
| WO | 00135595 | 3/2000 |
| WO | 2004098421 | 11/2004 |
| WO | 2004100805 | 11/2004 |

OTHER PUBLICATIONS

International Search Report for PCT/IB2007/004072 dated May 28, 2008.

State Intellectual Property Office of the People's Republic of China, Notification of the First Office Action for "Holder for a Surgical Reamer and Single Use Flat Reamer", dated Feb. 17, 2011.

* cited by examiner

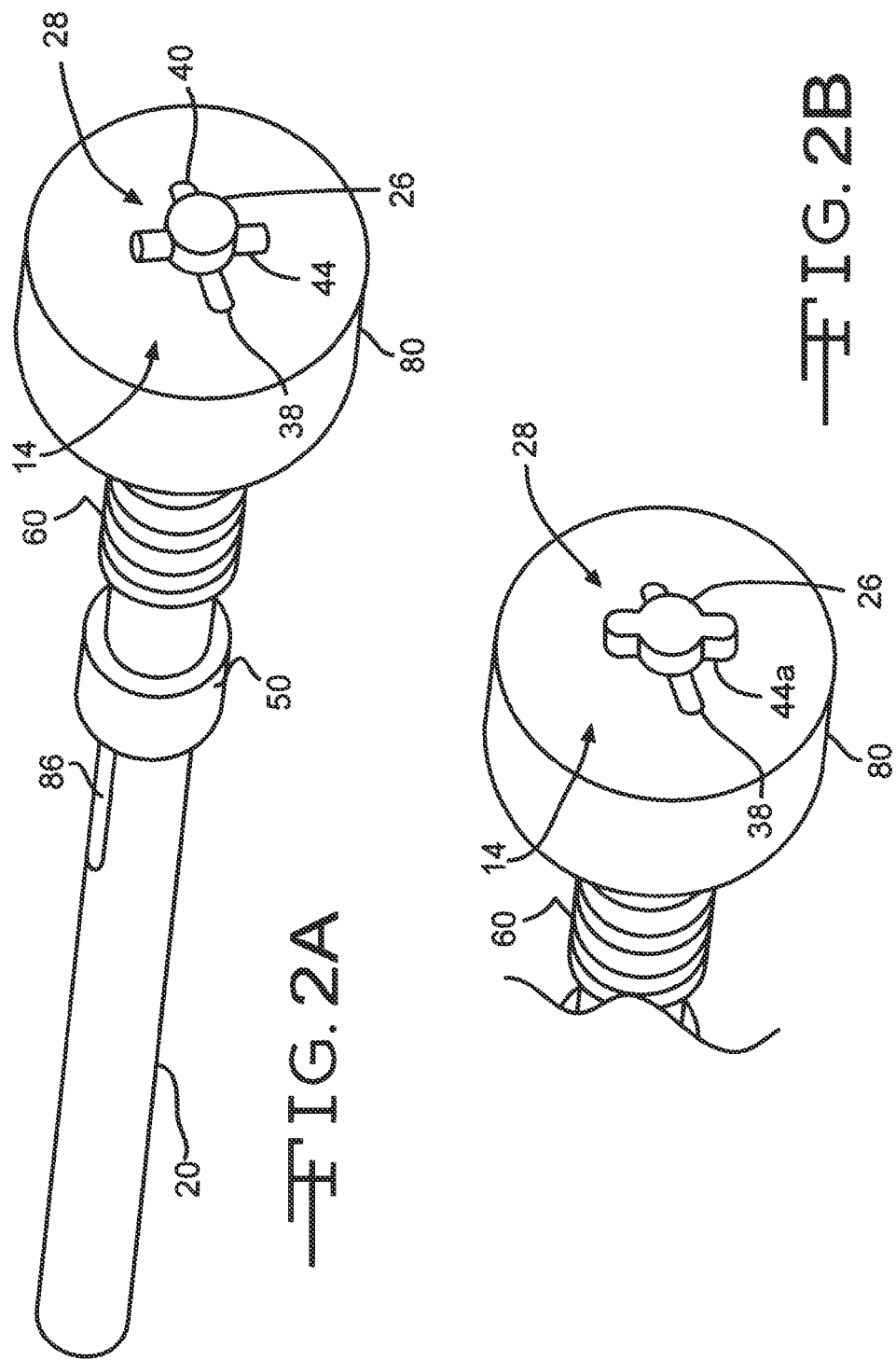

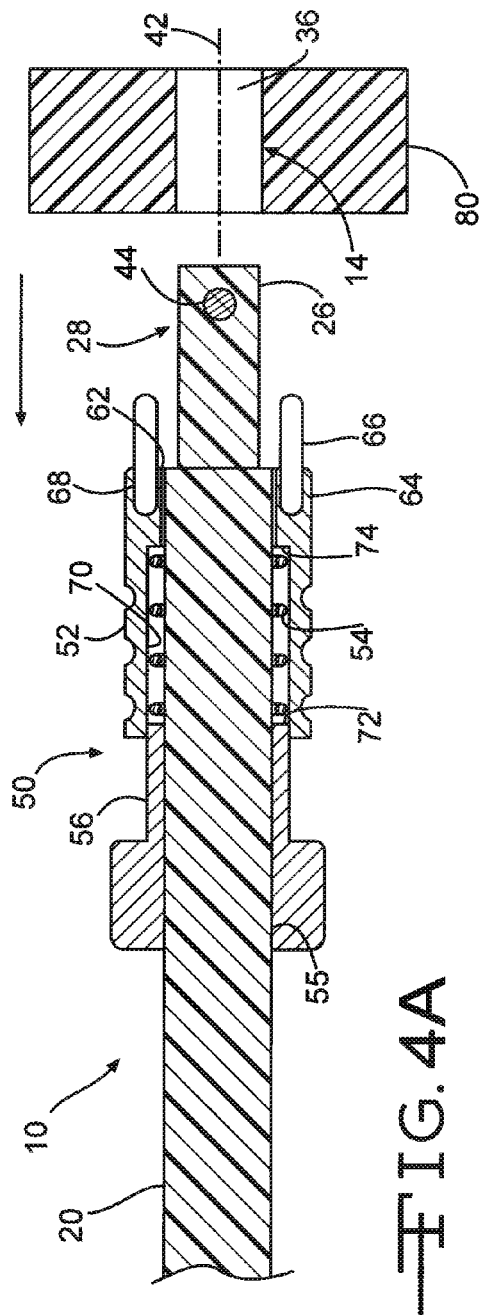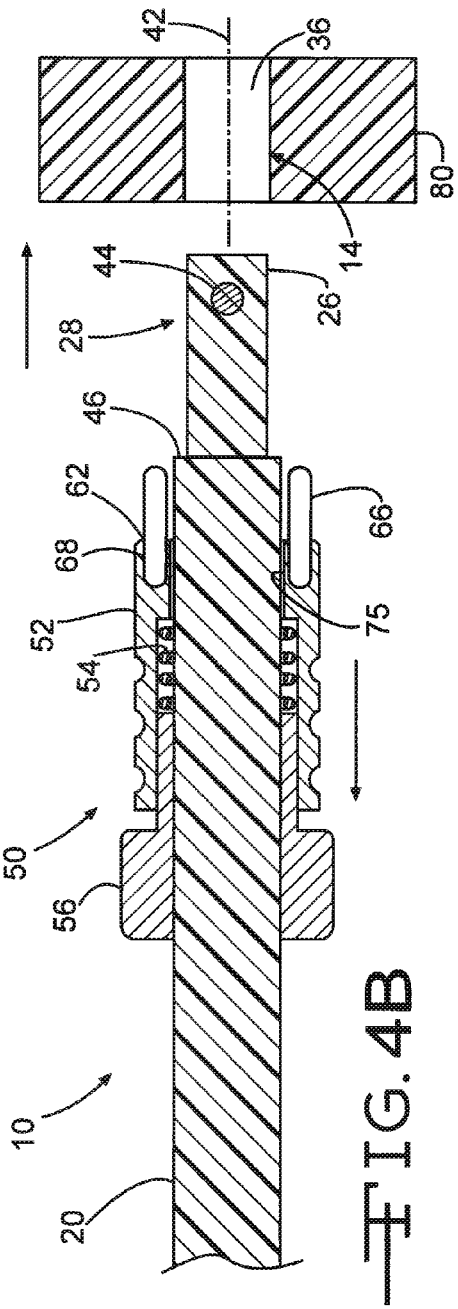

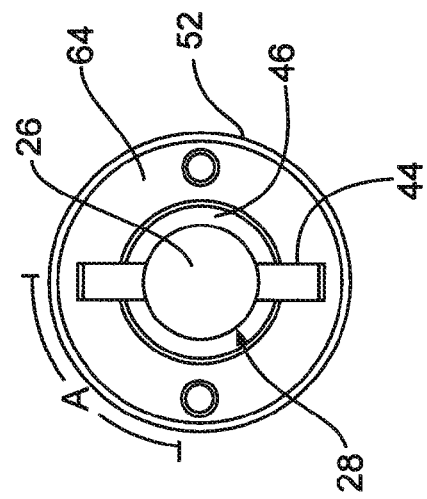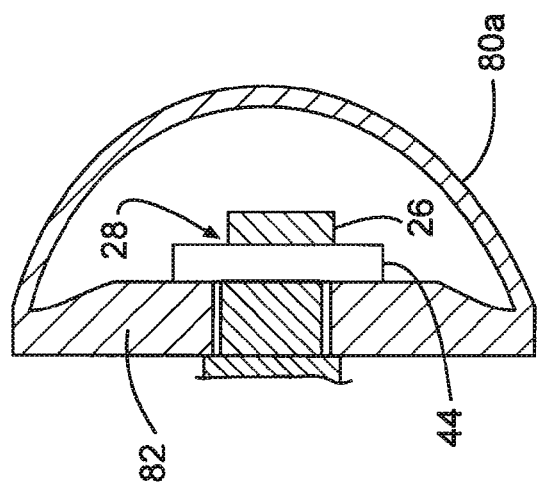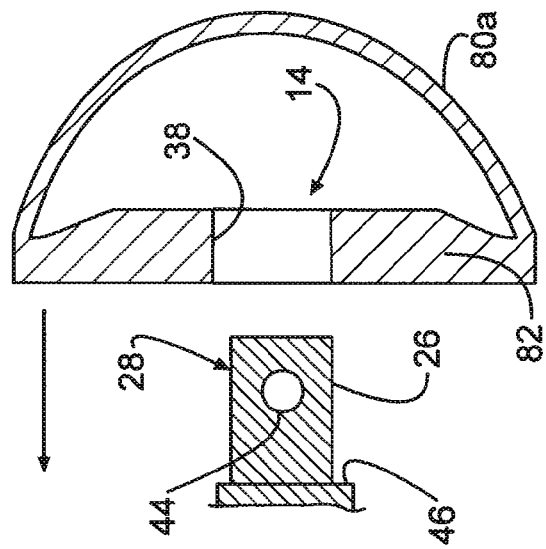

SURGICAL TOOL HOLDER AND SURGICAL TOOL

CROSS REFERENCE TO RELATED APPLICATIONS

This application claims priority to U.S. provisional application Ser. No. 60/882,247, filed Dec. 28, 2006 and Ser. No. 60/871,406, both of the same title, filed Dec. 21, 2006, the contents of which is incorporated herein by reference thereto.

BACKGROUND OF THE INVENTION

This invention relates to surgical instrument holders, and more particularly, to hand-held holders of rotary surgical cutting tools.

This invention relates to surgical instrument holders, and more particularly, to an instrument holder for a surgical instrument, comprising a shank equipped with a head designed to receive an instrument, and an annular locking component mounted so as to slide about the shank, under the head, equipped with locking means which cooperate with the head so as to lock the instrument on the head, and pushed against the head by a helical spring.

Surgical instruments and their respective holders have to be kept clean and sterile before any use in a hospital environment in order to minimize risk of transfer of disease or infection from patient to patient following the emergence of certain "prions" that are not killed by normal hospital sterilization and thus need to be physically removed through washing and rinsing. A surgical instrument, for example for preparing for the fitting of a hip prosthesis, works in a medium which causes considerable soiling of the instrument and of the instrument holder. Despite the importance of doing so, the thorough cleaning of these devices is difficult. Surgical instrument holders of the prior art are designed such that washing and rinsing are generally not an effective way of cleaning the instrument. This is due to the small spaces left between component parts which allow only minimal access by cleaning agents.

Instrument holders seeking to solve these problems include U.S. Pat. Nos. 5,658,290, 5,236,433, and 6,264,647 to the inventor, the contents of which are incorporated by reference. Such holders are designed to interface with a metal bar on an acetabular reamer, which is not conducive for use with disposable reamers in which the interface is insert molded of a plastic material. Further, the interface with such reamers is relatively large and therefore, limits the ability of the designer to provide a holder which is small and therefore more adapted for application in minimally invasive surgery.

Further, surgical instruments are generally improved when it is more readily apparent the state they are in, whether locked or unlocked.

What is needed therefore is a surgical instrument holder which is quickly and simply disassembled for cleaning and sterilization.

What is needed therefore is a surgical instrument holder adapted for interfacing with an insert-molded plastic base of a reamer.

What is needed therefore is a surgical instrument holder which is small and suitable for use in minimally invasive surgery.

SUMMARY OF THE INVENTION

A surgical tool holder and tool system is provided. The system includes the tool holder which has a center rod with a first shank end and a second tool end. The tool end has disposed thereon a tool interface. The tool support has an interface receiver engageable with the tool interface and the tool support for mounting a surgical tool head. The system further includes a quick connect mechanism disposed on the center rod proximate the tool interface. This mechanism is disposed to normally bear against the tool support when the tool support is engaged with the tool interface and securely hold the tool support to the tool holder.

The object of the invention is to enable quick disassembly for cleaning and component sterilization.

Another object of the invention is to provide a surgical instrument holder adapted for interfacing with an insert-molded plastic base of a reamer.

Another object of the invention is to provide a surgical instrument holder which is small and suitable for use in minimally invasive surgery.

Another object of the invention is to provide a surgical instrument holder that more clearly indicates that it is locked or unlocked.

BRIEF DESCRIPTION OF THE DRAWINGS

The attached drawings show embodiments of the invention by way of example.

FIGS. 2A and 2B are perspective views of the present quick connect system embodied as in FIG. 1, and illustrating alternative tool interfaces of (A) bayonet pins and (B) a T-bar.

FIG. 4A is a partial cross-sectional view of the present surgical tool holder as in FIG. 3A, but showing the quick connect mechanism prior to attachment of the tool support of a tool head to the tool shaft, and illustrating the normally engaged condition of the connect mechanism.

FIG. 4B is a partial cross-sectional view of the present surgical tool holder as in FIG. 4A, but showing the quick connect mechanism upon removal of a tool support from the tool shaft, and illustrating disengagement of the connect mechanism.

FIGS. 5A and 5B are partial cross-sectional views of the tool interface at the tool end of the center rod and its relationship with the interface receiver integral to an alternative tool support configuration.

FIG. 5C is an end view of the tool interface and quick connect mechanism at the tool end of the holder, and additionally illustrates that the angular relationship of the stop projection pins on the shaft to the engagement fingers on the ram relative to the radius of the shaft is fixed.

DETAILED DESCRIPTION OF THE PREFERRED EMBODIMENT(S)

Figure 1:
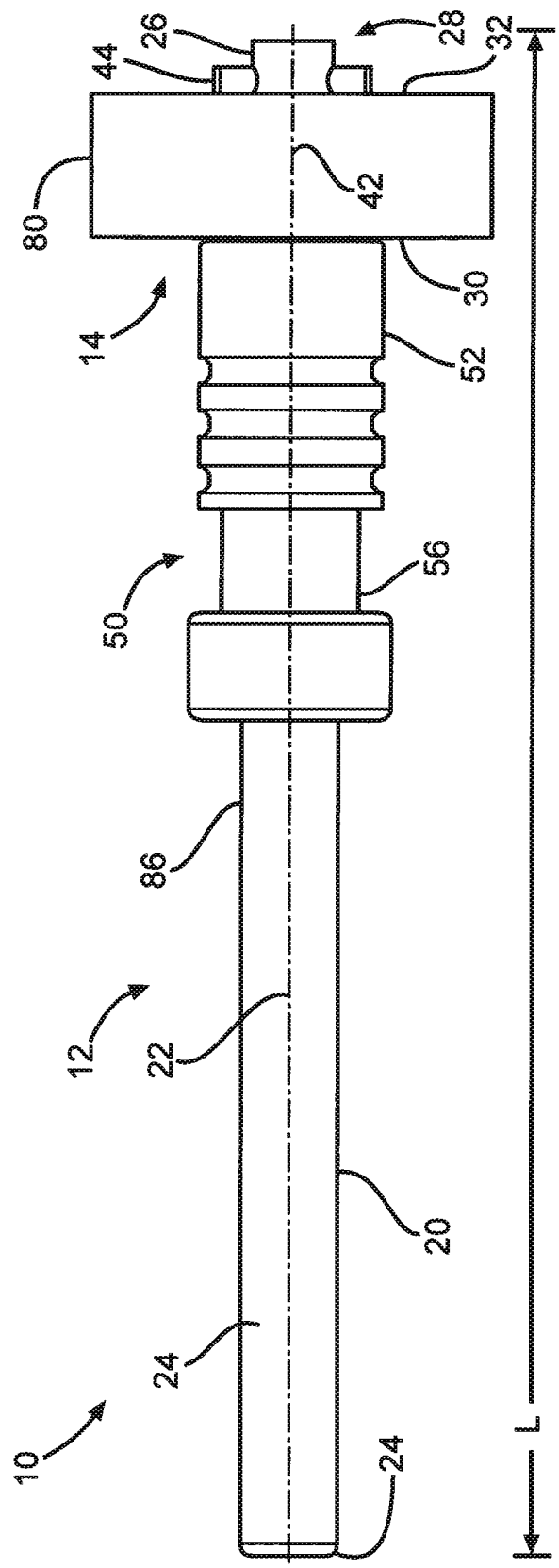
FIG. 1 a side plan view of the present embodied as a combination of a wheel-type tool surgical tool head attached to the tool holder.

Referring now to the drawings, the details of preferred embodiments of the present invention are graphically and schematically illustrated. Like elements in the drawings are represented by like numbers, and any similar elements are represented by like numbers with a different lower case letter suffix.

The present invention is an easy breakdown surgical tool holder adapted to engage with a tool support 14. A system 10 of the invention includes the tool support 14. Additionally, the present invention in a preferred embodiment includes an exemplary adaptation for a cannulated surgical tool. As illustrated in FIG. 1, the present system 10 includes a tool shaft 12 having a first shank end 24 and a second tool end 26 at which a tool interface 28 is disposed. The tool interface 28 passes through an interface receiver 36 integral to a tool support 14 (see FIGS. 4A and 4B). The tool support 14 may be integral with a surgical tool head 80, and is a structural feature of the present system 10 of the invention that supports the structure of the surgical tool head 80 in communication with the tool holder 12. The tool holder 12 can be partially broken-down or dissembled without having to remove component parts completely from the rest of the holder. The present invention is "easy breakdown" in that the tool holder 12 is easily put into its partially dissembled configuration which exposes the components of the holder 12 for proper cleaning and sterilization without risk of components parts becoming separated and lost.

The tool holder 12 has a center rod 20 with a linear axis 22. The tool holder 12 has a first shank end 24 and a second tool end 26. The shank end 24 may be adapted for attachment to a surgical tool drive or tool handle (not shown). The tool end 26 is adapted to have a tool interface 28 disposed thereon. The tool interface 28 is configured to mate with an interface receiver 36, which is incorporated into the tool support portion 14 of the surgical tool head 80, as shown in FIGS. 2A and 2B. Any type of surgical tool head 80 can be used with the present system 10 that appropriately incorporates an interface receiver 36 as taught herein. Examples of other surgical tool heads 80 are set forth in the figures.

Figure 3A:
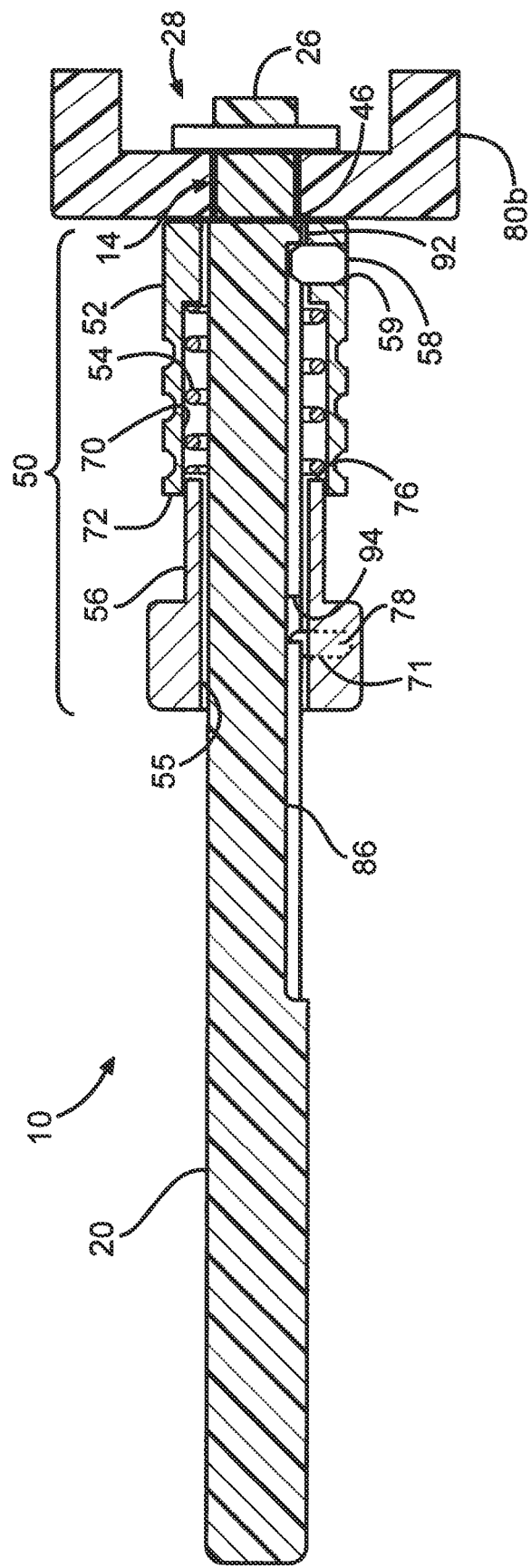
FIG. 3A is a partial cross-sectional side view of the present quick connect system showing the quick connect mechanism in an engaged condition with the toot support mounted on the tool holder, and the relationship of the ram pin and the guide pin to the tracking groove.
Figure 6:
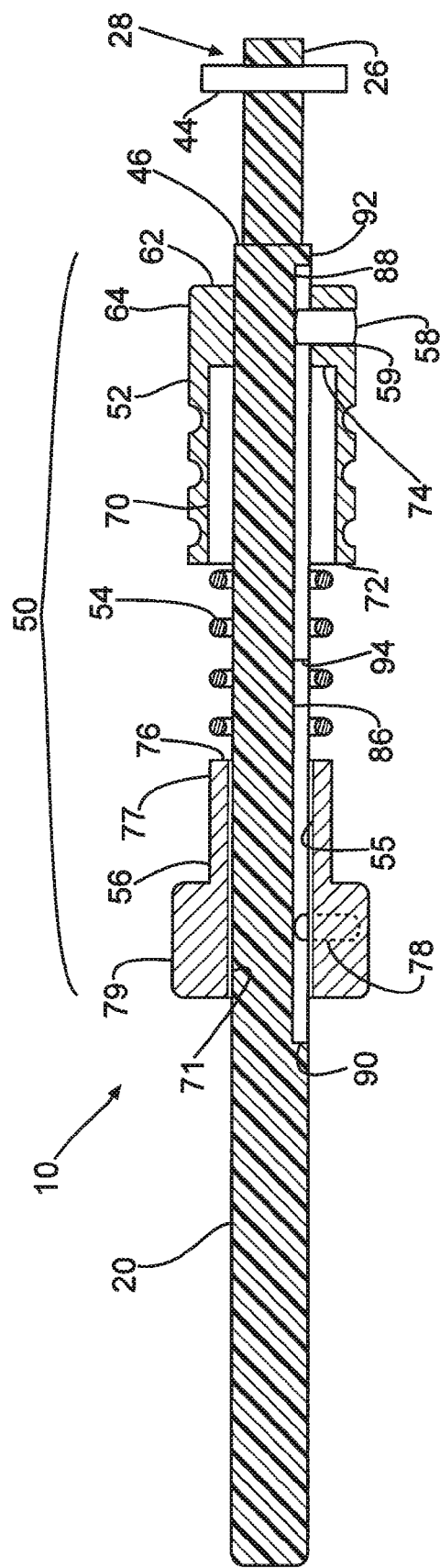
FIG. 6 is a partial cross-sectional side view of the present surgical tool holder, but in a partially dissembled condition illustrating the easy break-down feature on the present invention which allows cleaning and sterilization without having to fully separate any of the component parts from the tool shaft.

As shown in FIG. 3A and FIG. 6, the center rod 20 has a tracking groove 86 inset in its surface. The tracking groove 86 runs parallel to the linear axis 22 of the center rod 20 from a first groove end 88 proximate the tool end 26 of the center rod 20 to a second groove end 90 distal from the tool end 26. The first groove end 88 of the tracking groove 86 has a ram stop 92. Additionally, the tracking groove 86 has a release slot 94 disposed approximate a middle portion of the tracking groove 86. The release slot 94 communicates with the tracking groove 86 and is a component of the release fitting 95. The release fitting 95 comprises a combination of the guide pin 78 and release slot 94. In the preferred embodiment the release slot was configured as a single "J"-slot, but could be a double J-slot, a "T"-slot or the like.

Figure 3B:
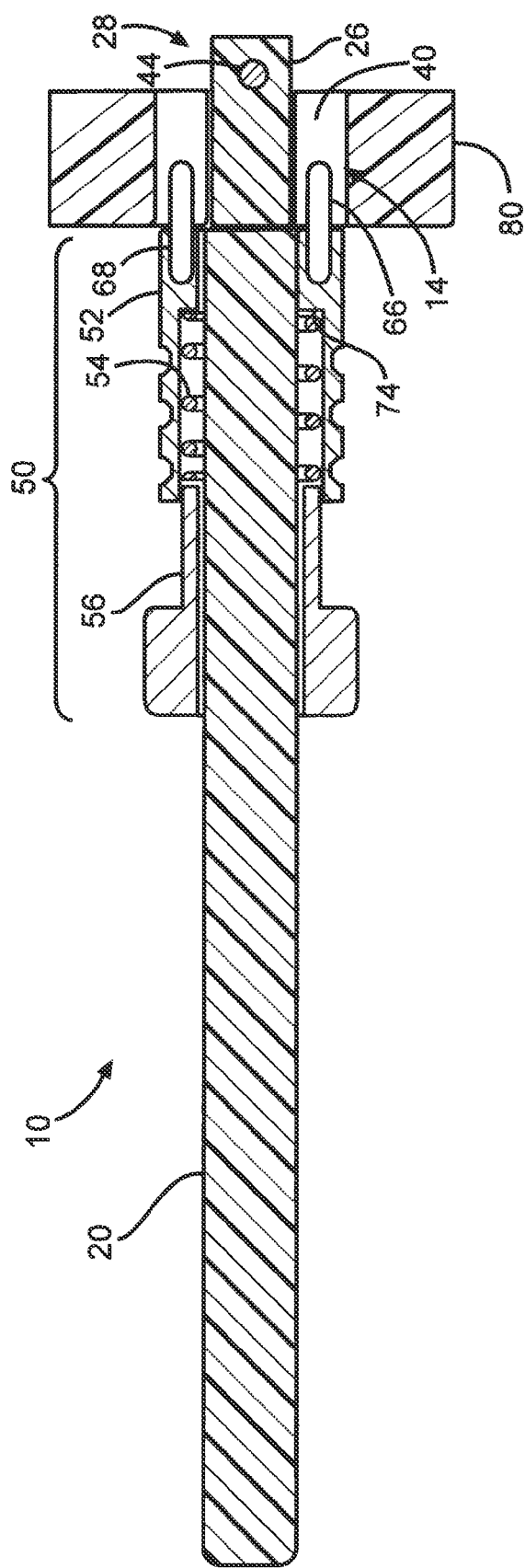
FIG. 3B is a partial cross-sectional bottom view of the present surgical tool holder showing the quick connect mechanism in an engaged condition with a tool support of an alternatively configured tool head, and illustrating the relationship of the engagement fingers to the tool interface receiver of the tool support.

As illustrated in the figures, the interface receiver 36 is integral with the tool support 14. The interface receiver 36 is configured to pass the tool interface 28 and to mate with engagement protrusions, in this case fingers 66 which project from the ram face 62 of the ram 52. See FIG. 3B. In the preferred embodiment illustrated, the interface receiver 36 comprised a rod bore 38 which passed through the tool support 14 from its back surface 30 to its front face 32. The rod bore 38 is disposed to closely but slidably receive the tool end 26 of the center rod 20. Two slot ears 40 were disposed radially to the bore axis 42 of the rod bore 38. Although the embodiment illustrated had two slots ears 40, it is anticipated that fewer or more slot ears 40 may be practiced in the present system 10. The bore axis 42 is coaxial with the linear axis 22 of the center rod 20. The slot ears 40 allow transversely extending projections 44, which extend radially outward, beyond a diameter of the center rod 20, to pass through the interface receiver 36 when the tool end 26 of the center rod 20 is slid through the rod bore 38. The tool head 80 is slid onto the tool end 26 of the center rod 20 until its back surface 30 contacts the rod shoulder 46 (see FIGS. 3A and 5C). In the embodiment illustrated, the stop projections 44 were the ends of a cross-pin disposed at the second tool end 26 of the center rod 20. Alternatively, the stop projections can be a "T"-bar fitting 44a disposed at the second tool end of the center rod, as shown in FIG. 2B.

Once the stop projections 44 of the tool interface 28 were passed through the interface slot ears 40 of the interface receiver 36, the tool head 80 was rotated 90 degrees about the tool end 26 of the center rod 20 and the quick connect mechanism 50 allowed to securely engage the interface receiver 36 and bear against the back surface 30 of the tool support 14. The quick connect mechanism 50 is disposed proximate the tool interface 28 at the tool end 26 of the center rod 20. The connect mechanism 50 is disposed to normally bear against the back surface 30 of the tool support 14 when the front surface 32 of the tool support 14 is engaged with the tool interface 28. See FIG. 2 and the further explanation below.

The tool support 14 is an important feature of the present holder system 10, the support being integrated into a surgical tool head 80. In FIGS. 2A and 2B, the tool head is illustrated as a disk-shaped tool, such as a grinder wheel, and the tool support 14 is integral to the tool head 80. However, the particular structure and function of the tool head 80 is not a part of the present invention. Further, it is clear to one of ordinary skill in the art that the present tool support 14 may be incorporated into a number of different tool heads 80 and be practicable in the present system 10. For example, FIG. 3A illustrates a tool head 80b that is a slight variation of the tool head 80 of FIG. 3B, but which still has the tool support feature 14 of the present system 10. A further example is illustrated in FIGS. 5A and 5B, where the tool support 14 comprises a component of a dome-shaped tool 80a, e.g., a hemispherical grinder. In this embodiment, the tool support 14 is incorporated into the base member 82 of the dome-shaped tool 80a.

The quick connect mechanism 50 on the surgical tool holder 12 is also an important feature of the present quick connect system 10. As shown in FIGS. 3A to 4B, the connect mechanism 50 comprises a ram 52, a collar 56 and a bias member 54, all of which are slidably received about the center rod 20 approximate its tool end 26. The ram 52 is disposed proximate the tool end 26 of the center rod 20. The ram 52 has a ram bore 60 through which the center rod 20 slidably passes. The ram 52 has a ram face 62 disposed on a first ram end 64. At least one engagement finger 66 projects from the ram face 62 parallel to the linear axis 22 of the center rod 20. In the embodiment illustrated, two engagement fingers 66 were fixed in finger receptacles 68 set into the ram face 62 of the ram 52.

The ram 52 has an internal chamber 70 open to a second ram end 72. The internal ram chamber 70 has a bottom seat 74 which interfaces with the bias member 54. A locking pin 58 projects from the ram bore 75 into the tracking groove preventing the ram 52 from rotating about the linear axis 22 of the center rod 20, while allowing it to be slidable on the center rod 20 along the linear axis 22. The locking pin 58 is set into a stop pin receptacle 59 proximate the ram face 62 of the ram 52. The locking pin 58 may be set into the stop pin receptacle 59 by any of a number of means known to the ordinary skilled artisan for setting such pins. For example, the locking pin 58 can be a set screw and the pin receptacle 59 having complementary threads.

A biasing member 54 is slidably disposed around the center rod 20 between the collar 56 and the ram 52. The biasing member 54 is receivable into the internal chamber 70 of the ram 52. A first bias end of the bias member is received against the bottom seat 74 of the ram 52. The second bias end of the biasing member 54 is received against the bias face 76 of the collar 56. In the illustrated embodiment, the bias face 76 of the collar 56 was receivable into the internal chamber 70 of the ram 52. In the embodiment illustrated in the figures, the biasing member 54 was a single helix coil spring. However, alternative biasing members are known to and selectable by one of ordinary skill in this field for practice in the present system 10. For example, a double helix coil spring or other elastic member could be used, so long as it can be appropriately cleaned and sterilized.

The collar 56 has a collar bore 55, through which the center rod 20 slidably passes. The collar 56 also has a bias face 76 at a first collar end 77 and a guide pin 78 projecting into the collar bore 55 proximate a second collar end 79. The guide pin 78 is set into a guide pin receptacle 71 in a manner similar to that of the stop pin and its receptacle 58 and 59 of the ram 20. The guide pin 78 is slidably received into the tracking groove 86, which allows the collar 56 to be slid back and forth along the center rod 20 within the limits of the tracking groove 20. Once the holder 12 is assembled for use, a tool head 80 may be attached to the quick connect mechanism 50. To assemble the holder from its broken down configuration (see FIG. 6) for use to hold a tool head 80, the collar 56 is slid toward the tool end 26 of the center rod 20. This pushes the bias member 54 and the ram 52 before it, until the ram 20 is stopped by the locking pin 58 impinging against the ram stop 92. Once the ram 20 is against the stop 92, the bias member 54 is forced against the bias seat 74 of the ram 54 by further movement of the collar 20 toward the tool end 26 of the center rod 20. This forces the collar face 76 against the bias member 54 causing it to compress and exert a bias against the ram 20, holding the ram 20 against the ram stop 92. The collar 56 is forced further forward against the bias force until the guide pin 78 is adjacent and receivable into the J-slot 94. The collar 56 is then rotated so as to set the guide pin 78 in the J-slot 94 and have it retained there by the bias force of the bias means 54 being compressed between the bias seat 74 of the ram 52 and the collar face 76 of the collar 56. The resulting bias force is maintained by the guide pin 78 of the collar 56 being engaged and retained in the J-slot of the tracking groove 86. The bias force locks the collar 56 in position along the length L of the center rod 20 and biases the ram 20 into its normally engaged configuration.

To disengage the tool interface 28 from the tool support 14 and remove the surgical tool head 80 from the holder 12, the ram 52 is drawn back toward the shank end 24 of the center rod 20 to disengage (withdraw) the fingers 66 from the interface receiver 36. Once the fingers 66 are withdrawn from the ear slots 40 of the interface receiver 36, the tool support 14 can be rotated to align the stop projections 44 with the ear slots 40 and the tool support 14 and integral tool head 80 can be separated from the holder 12 (see FIG. 4B).

To break-down or partially dissemble the holder 12 for cleaning and sterilization, the collar 56 is rotated to remove the guide pin 78 from the J-slot 94. Once the guide pin 78 is released from the J-slot, the collar 56 may be slid on the center rod 20 along the tracking groove toward the second groove end 90 of the tracking groove 86. With the collar 54 released from the J-slot, the bias member 54 may be removed from the internal chamber 70 of the ram 52 and all three elements: the ram 52, the bias member 54 and the collar 56 can be spread out along the length of the tracking groove 86 on the center rod 20 to facilitate their cleaning and sterilization. See FIG. 6. In this configuration, none of the components parts of the holder 12 are separated from the device as a whole. In this manner, release of the guide pin 78 from the J-slot 94 allows partial disassembly of the connect mechanism 50 of the holder 14 to provide the easy break-down feature of the present system.

Figure 7A:
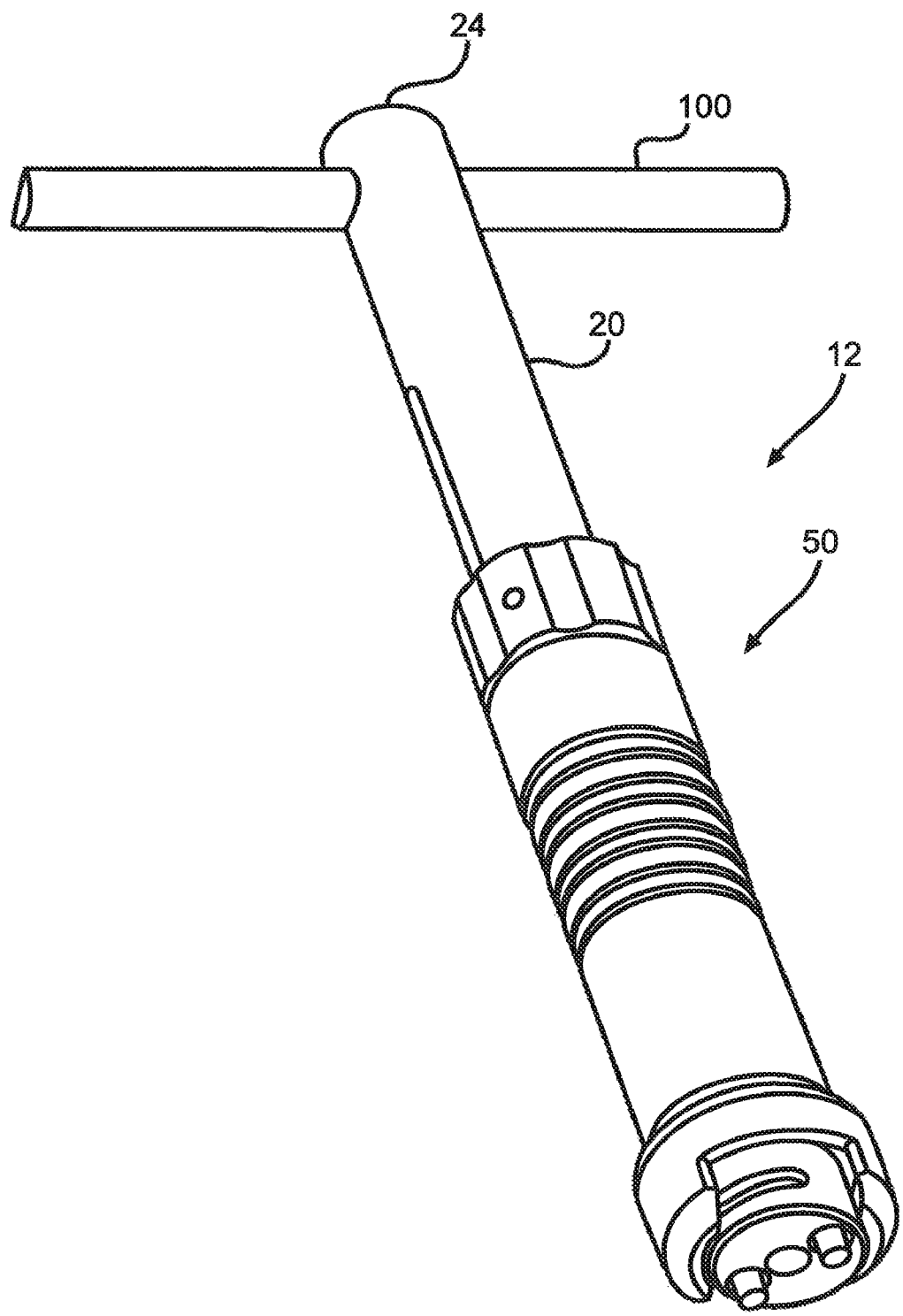
FIG. 7A is a perspective view of an alternative preferred embodiment of the present surgical tool holder having a handle attached to the drive end of the tool shaft, which handle provides both a stop/retainer for the easy disassembly feature and as a manual grip for using the tool for its intended purpose.
Figure 7B:
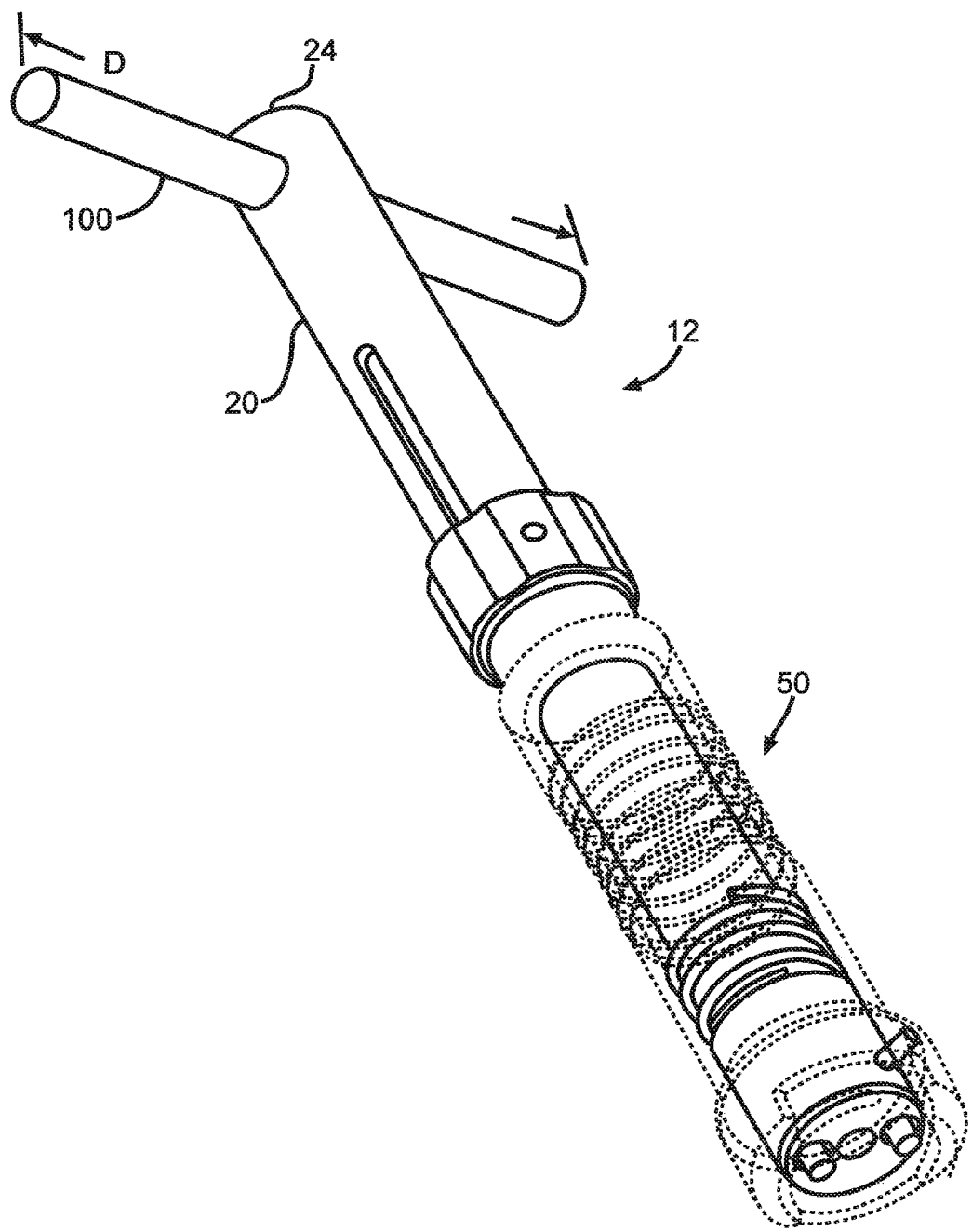
FIG. 7B is a partial phantom perspective view of the drive portion of the quick connect system of the tool holder of FIG. 7A.

As illustrated in FIGS. 7A and 7B, in a preferred embodiment, shaft 12 of the present surgical tool holder 12 has a grip or handle 100 attached to the drive end 24 of the tool shaft 12. The grip or handle 100 has a dimensions which is at least sufficiently larger than the cross-section of the collar bore 55 to prevent the collar 56 from passing over the handle 100. This feature of the holder 12 enables the configuration wherein none of the components parts of the holder 12 are separated from the device as a whole upon release of the collar 56 from the retainer-slot 94. The handle thus provides a stop feature on the holder 12 which enables partial disassembly of the connect mechanism 50 of the holder 14 to provide the easy break-down feature of the present system. Additionally, the handle 100 provides a manual grip for using the tool for its intended purpose.

Figure 8A:
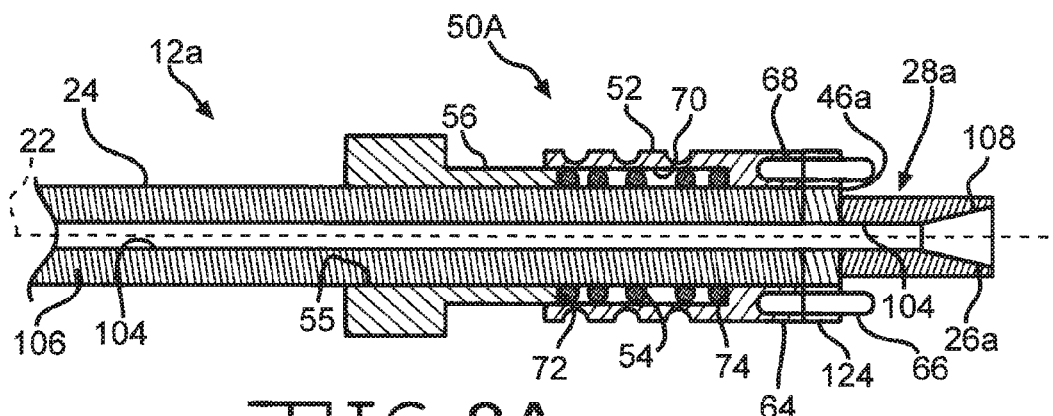
FIG. 8A is a cross sectional view of another embodiment of the tool holder of the invention, in a lock position.
Figure 8B:
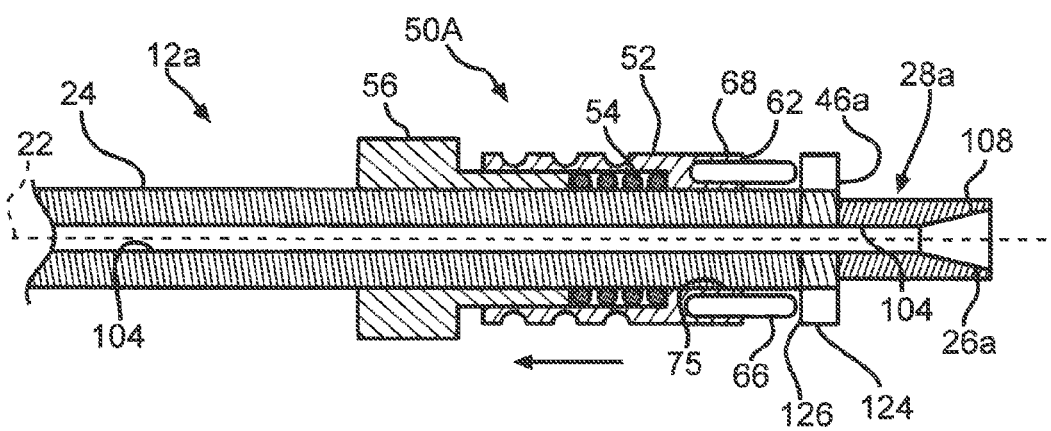
FIG. 8B is a cross sectional view of the embodiment of FIG. 8A in an unlocked position.
Figure 8C:
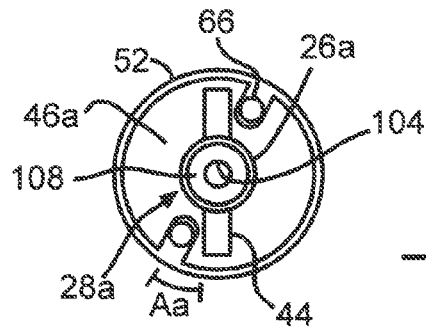
FIG. 8C is a front view of the embodiment of FIG. 8A.

As illustrated in FIGS. 8A to 8C and 9A to 9E, in preferred embodiment of the present surgical tool holder 12a and surgical tool 10a, the surgical tool holder 12a and tool support quick connect mechanism 50a are combined with a tool support 14a that is adapted to a cannulated surgical tool 80c. In the examples illustrated, the center rod or shaft 20a has a shaft through bore 104 passing along its length L. The shaft through bore 104 has an opening at one end at the axis 22 of the tool end 26a and at the other end at an access port 106 toward the shank end 24 of the center rod 20a. In FIG. 8A, the access port 106 is radial to the axis 22 and opens on to the circumference of the center rod 20a. In FIG. 8B, the access port (not shown) is co-axial with the axis 22 and opens at the shank end 24 of the center rod 20a. The shaft through bore 104 is disposed to co-axially mate with the cannula (not shown) of the cannulated surgical tool 80c as described below. The tool end 26a of the center rod 20a. has a countersunk recess 108 inset in it.

As illustrated in FIGS. 9A to 9E, the cannulated surgical tool 80c has a tool support 14a integral to the surgical tool 80c. The interface receiver 116 of the tool support 14a is configured to receive the tool interface 28a and to mate with the engagement fingers 66 projecting from the ram face 62 of the ram 51a. See FIG. 9A. In this embodiment, the quick connect mechanism 50a is disposed to normally biased in a forward direction, to bear against the back surface 126 of the shoulder member 124. See FIG. 8A. The bayonet-fitting slots 114 allow the stop projections 44 of the tool interface 28a to be aligned with and to pass into the interface receiver 116 when the tool end 26a of the center rod 20a is slid into the rod bore 118 of the cannulated tool head 80c. See FIGS. 9B and 9C. The tool head 80c is slid onto the tool end 26a of the center rod 20a until its back surface 120 contacts the rod shoulder 46a, as in FIG. 9D.

Figure 9A:
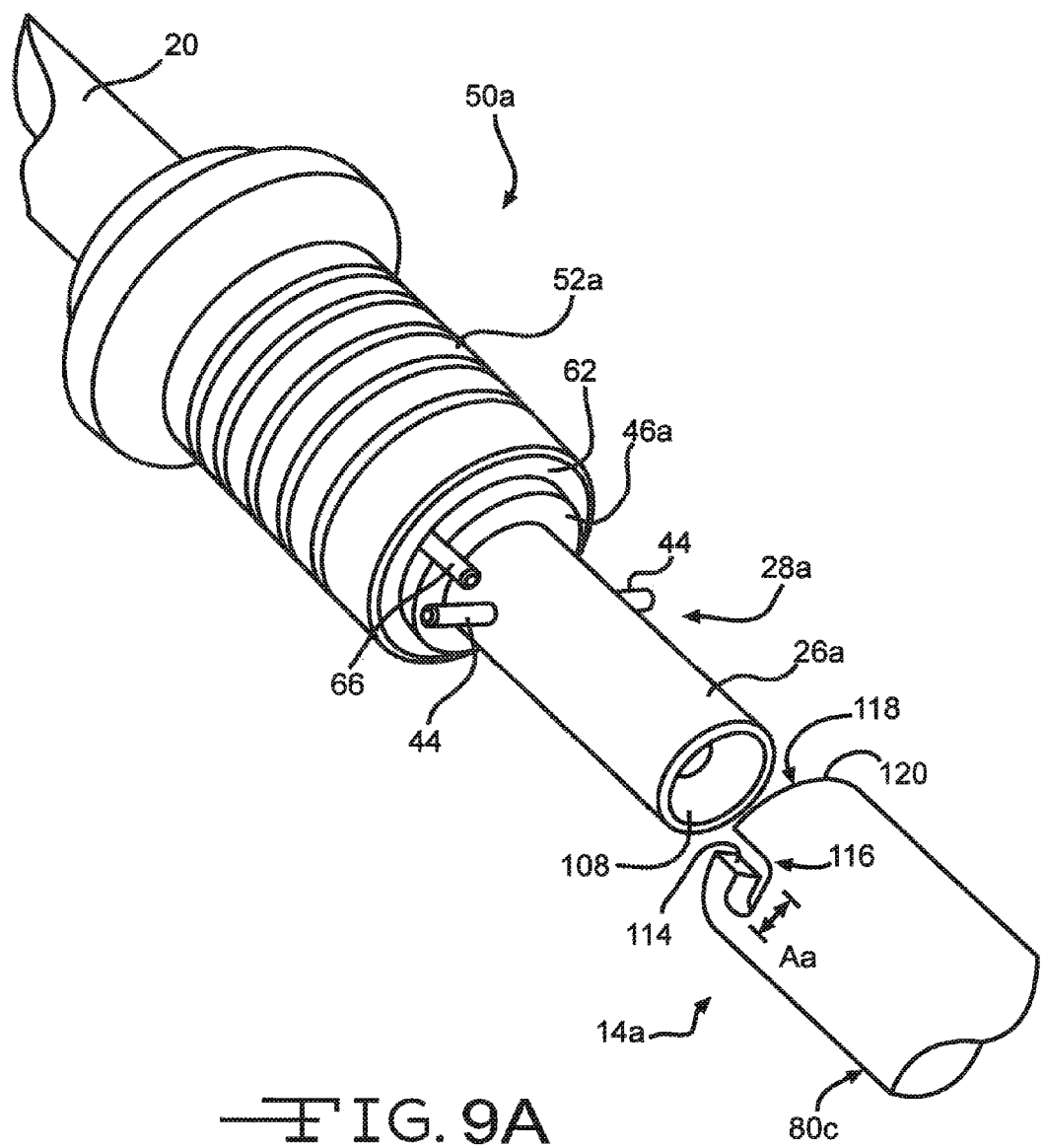
FIGS. 9A-9E are perspective views of the embodiment of FIG. 8A beginning in a partially disassembled position to an assembled position.
Figure 9B:
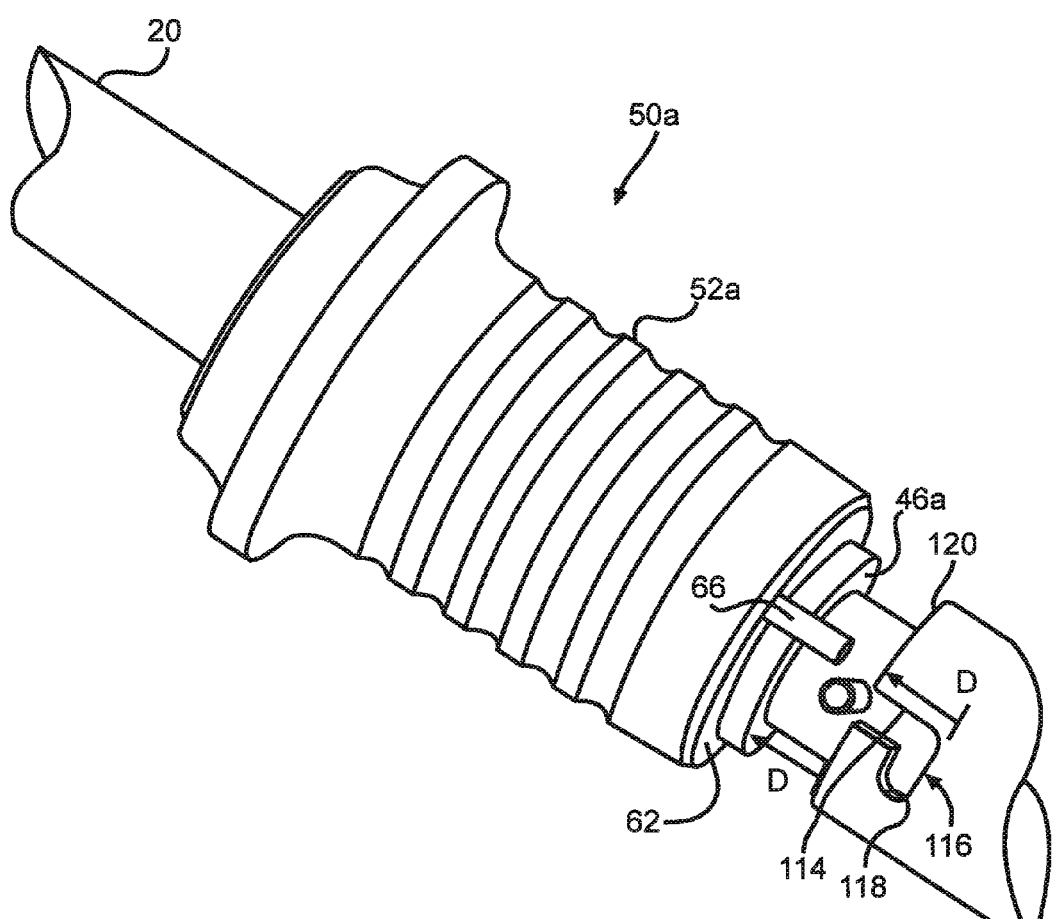
Figure 9C:
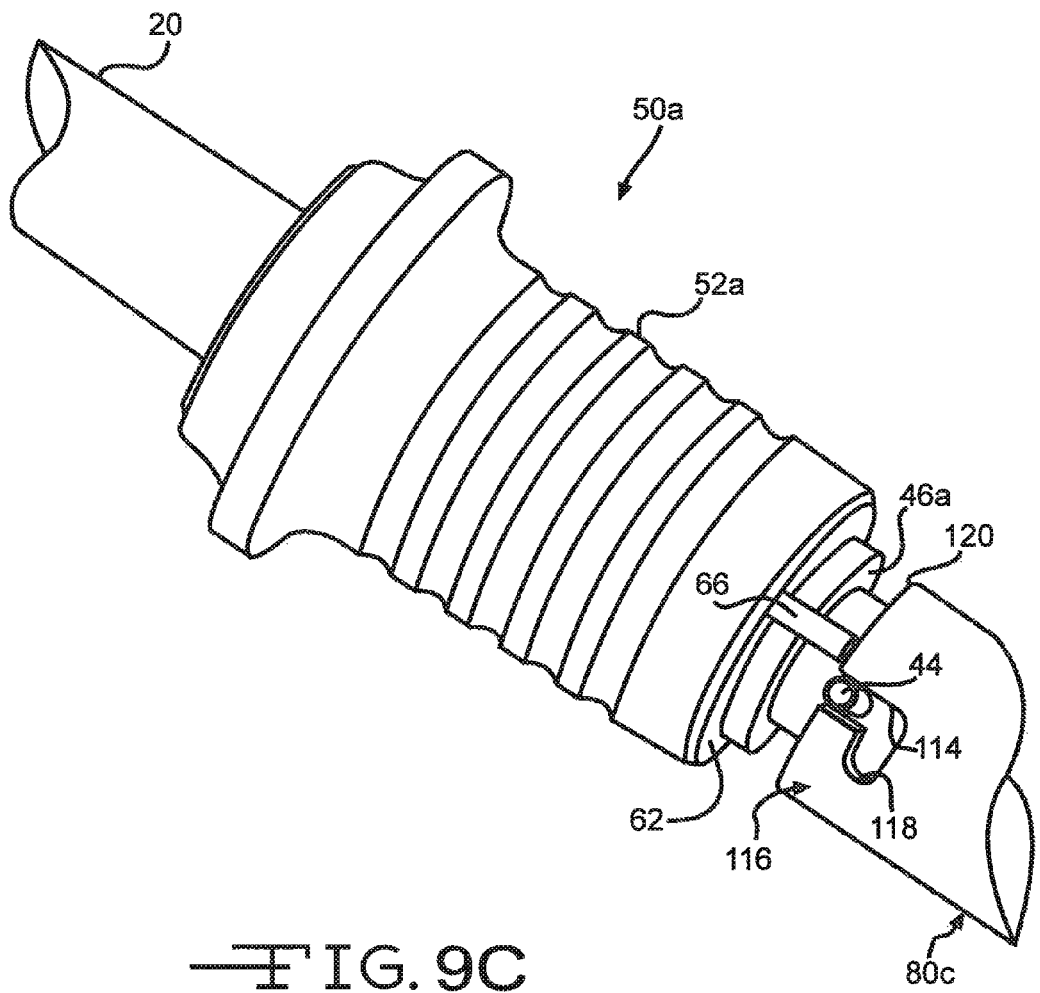
Figure 9D:
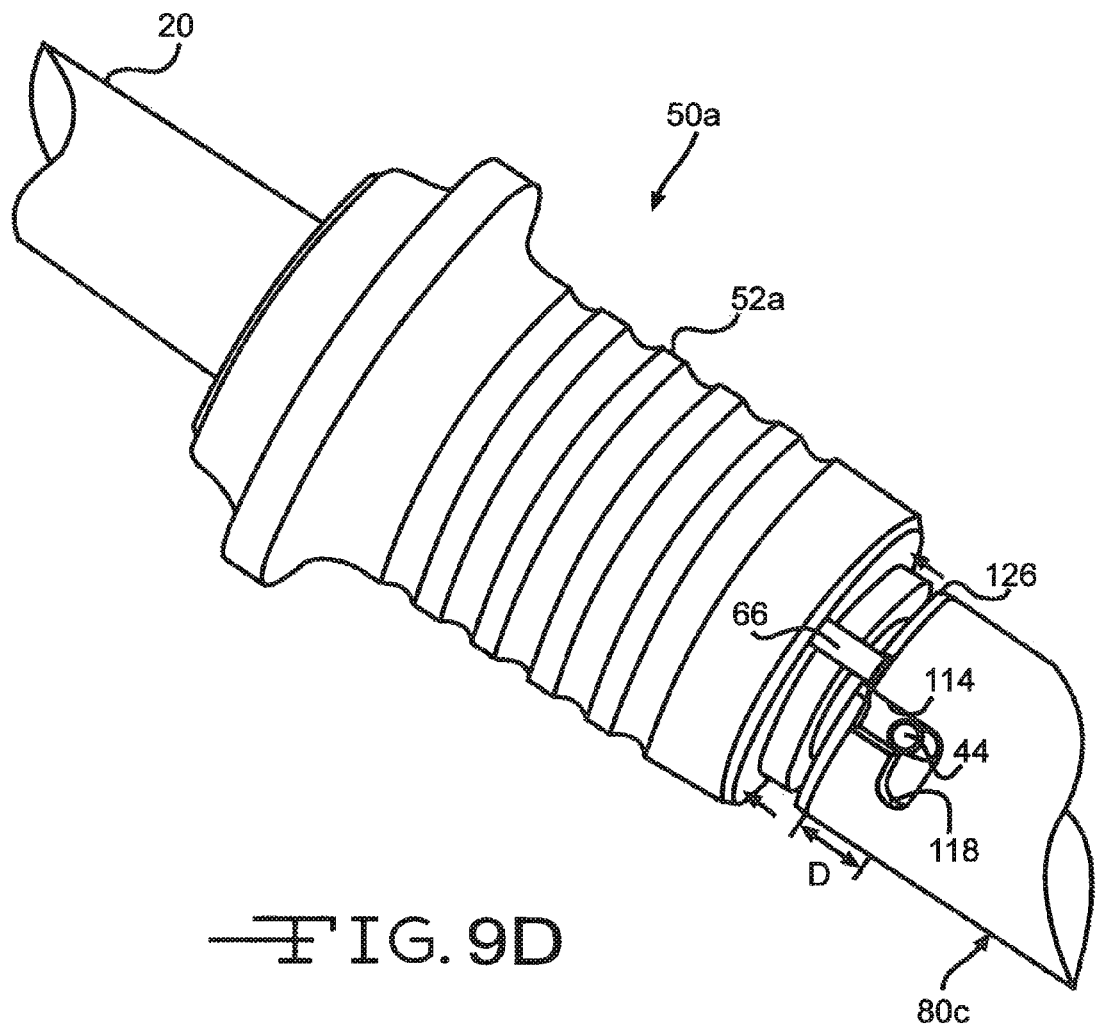
Figure 9E:
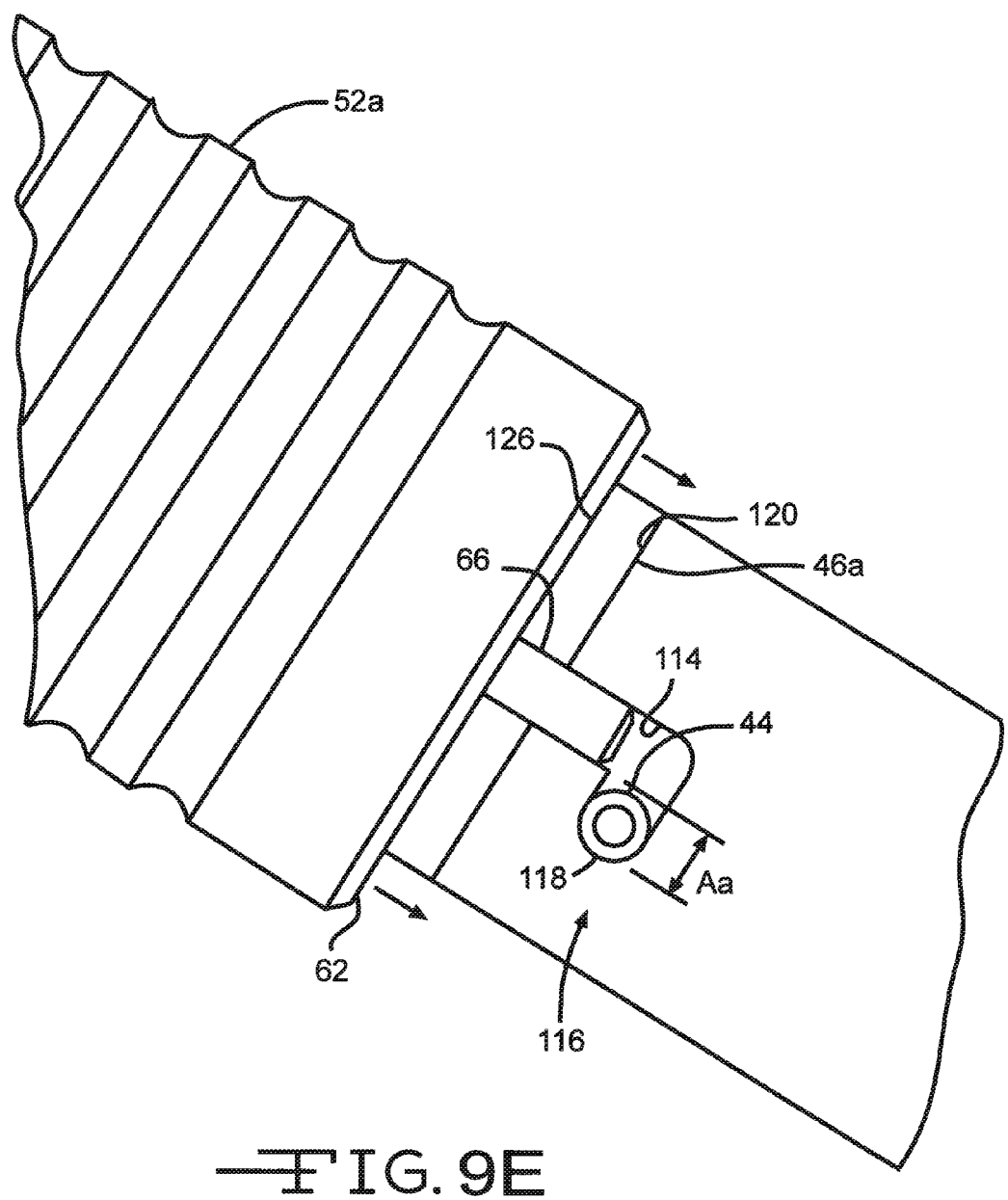

Referring to FIG. 9E, once the stop projections 44 of the tool interface 28a have passed the distance D into the interface slots 114 of the interface receiver 116, the tool head 80c is rotatable Aa degrees about the tool end 26a of the center rod 20a, so that the stop projections 44 engage the slot seats 118 of the interface slots 114. When the stop projections 44 engage the slot seats 118 after Aa degrees of rotation of the tool head 80c, the engagement fingers 66 projecting from the ram face 62 of the ram 51a are in alignment with the openings of interface slots 114. In this configuration, the normal bias on the ram 52a of the quick connect mechanism 50a can automatically drive the engagement fingers 66 the distance D into the interface slots 114. This action results in the cannulated tool head 80c to be securely fixed to the tool holder 12a. The cannulated tool head 80c is a surgical tool head typical in the field, but adapted to have the tool interface 28a of the present invention. Fixing of the the canulated tool head 80c to the tool holder 12a causes the cannula of the tool head (not shown) to be coaxially aligned with the shaft through bore 104 of the holder 12a. Release of the tool head 80c from the tool holder 12a is accomplished in substantially the same manner as described above.

The quick connect mechanism 50a has four pins 44, 66 on a tool interface 28a which guide and securely mate with the cannulated tool head 80c. The tapered or conical countersunk recess 108 provides an alignment guide for a guide wire or similar tool (not shown) to pass through the tool head 80c, the attached rod 24a, and out the access port 106. In use, the interface slots 114 of the tool head 80c are manually aligned with the engagement finger 44 of the tool interface 28a. Then the tool head 80c is pushed straight backward (see arrow in FIG. 8B) against the bias of the connect mechanism 50a. When the stop face 120 of the tool head 80c engages the shoulder face 46a, the tool head 80c is rotated Aa degrees, causing the normal bias on the ram 52a of the connect mechanism 50a to drive the engagement fingers 66 the distance D into the interface slots 114. This action results in the canulated tool head 80c being securely fixed to the tool holder 12a. In this configuration, the cannulated tool head 80c is fully captured by the tool holder 12a, and substantially secured against motion in all six degrees of freedom (3 translational and 3 rotational).

In an advantage, the invention provides for quick disassembly for cleaning and component sterilization. All parts come apart while being held loosely together so as to prevent loss of parts while providing access to all parts for a more thorough cleaning.

In another advantage, the surgical instrument holder is adapted for interfacing with an insert-molded plastic base of an acetabular reamer. This is because insert molding is best suited to applications where there are no thin, or elongated portions as exist in a cross-bar reamer interface (e.g., the cross bar itself, because it is elongated, is not well suited to insert molding).

In another advantage, the surgical instrument holder is small and suitable for use in minimally invasive surgery. The overall diameter of the coupling end of the reamer is small and so makes easier its insertion into a small incision, for coupling with a reamer in the body cavity.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A surgical tool holder adapted to connect to a surgical tool, the tool holder comprising:
    a) a center rod comprising a linear axis extending from a first, proximal shank end to a second, distal tool end;
    b) a tracking groove extending along a surface of the center rod parallel to the linear axis from a first groove end adjacent to the tool end to a second groove end proximate from the tool end, the tracking groove communicating with a release slot provided in the surface of the center rod at an intermediate location between the first and second groove ends;
    c) a tool interface comprising at least one transverse projection extending radially outwardly in a fixed manner beyond a diameter of the center rod proximate the distal tool end;
    d) a ram disposed proximate the distal tool end and comprising a ram bore receiving the center rod in a movable relationship therewith, wherein the ram comprises a first ram end from which at least one engagement finger projects parallel to the linear axis of the center rod, and an opposite, second ram end, wherein a locking pin supported by the ram projects into the ram bore and is movable along the tracking groove of the center rod;
    e) of a collar having a collar bore through which the center rod movably passes, the collar having a bias face at a distal collar end, wherein a guide pin supported by the collar projects into the collar bore and is movable along the tracking groove and the release slot of the center rod; and
    f) a biasing means positioned between the collar and the ram in a movable relationship about the center rod, the biasing means having a first bias end that is contactable by the ram and a second bias end contactable by the bias face of the collar,
    g) wherein the ram supported by the center rod and a surgical tool are relatively manipulatable to move the transverse projection into a locked relationship with a second slot of the surgical tool with the engagement finger blocking rotational movement of the surgical tool with respect to the tool holder, and wherein the collar is manipulatable along the center rod against the biasing means to align the guide pin with the release slot and then to move the guide pin into a locked relationship with the release slot of the center rod with the biasing means providing a biasing force against the ram preventing the transverse projection and the engagement finger from releasing from the surgical tool thereby locked to the connected tool holder, and h) wherein the collar is manipulatable to remove the guide pin from the release slot and then to move the guide pin along the center rod to relax the biasing means against the ram so that the ram supported on the center rod and the surgical tool are relatively manipulatable to move the engagement finger out of the second slot and to move the transverse projection out of the blocking relationship with the surgical tool thereby being separable from the tool holder.

2. The surgical tool holder of claim 1 wherein the tool interface comprises a cross-pin fitting providing the at least one transverse projection disposed at the second, distal tool end of the center rod.

3. The surgical tool holder of claim 1 wherein the tool interface comprises a "T"-bar fitting providing the at least one transverse projection disposed at the second, distal tool end of the center rod.

4. The surgical tool holder of claim 1 adapted to interface with a disk-shaped tool.

5. The surgical tool holder of claim 1 adapted to interface with a dome-shaped tool.

6. The surgical tool holder of claim 1 wherein a grip handle is disposed on the center rod proximate the shank end.

7. The tool holder of claim 1 wherein the shank end of the tool driver is adapted to connect to a tool driver.

8. The tool holder of claim 1 wherein the release slot is selected from the group consisting of a J-slot, a double J-slot, and a T-slot.

9. The tool holder of claim 1 wherein a through bore provided along the linear axis of the center rod extends from the proximal shank end to the distal tool end.

10. The tool holder of claim 9 wherein the through bore comprises an access port located adjacent to the proximal shank end and a countersunk recess at the distal tool end.

11. The tool holder of claim 1 wherein the center rod comprises a shoulder adjacent to the distal tool end, the shoulder providing a surface against which a surgical tool contacts when it is locked to the tool holder.

12. The tool holder of claim 1 wherein the ram comprises an internal chamber at the second ram end and the biasing means is at least partially receivable in the internal ram chamber when the collar is moved toward the ram.

13. The tool holder of claim 12 wherein the bias face of the collar is receivable into the internal chamber of the ram with the biasing means disposed therebetween.

14. A tool kit, which comprises:
a) at least one tool handle according to claim 1;
b) a plurality of surgical tools adapted to detachably connect to the tool handle; and
a case for organizing components of the kit.

15. A surgical tool holder adapted to connect to a surgical tool, the tool holder comprising:
a) a center rod comprising a linear axis extending from a first, proximal shank end to a second, distal tool end;
b) a tracking groove extending along a surface of the center rod parallel to the linear axis from a first groove end adjacent to the tool end to a second groove end proximate from the tool end, the tracking groove communicating with a release slot provided in the surface of the center rod at an intermediate location between the first and second groove ends;
c) a tool interface comprising at least one transverse projection extending radially outwardly in a fixed manner beyond a diameter of the center rod proximate the distal tool end;
d) a ram disposed proximate the distal tool end and comprising a ram bore receiving the center rod in a movable relationship therewith, wherein the ram comprises a first ram end from which at least one engagement finger projects parallel to the linear axis of the center rod, and an internal chamber open to a second ram end, wherein a locking pin supported by the ram projects into the ram bore and is movable along the tracking groove of the center rod;
e) a collar having a collar bore through which the center rod movably passes, the collar having a bias face at a distal collar end, wherein a guide pin supported by the collar projects into the collar bore and is movable along the tracking groove and the release slot of the center rod; and
f) a biasing means positioned between the collar and the ram in a movable relationship about the center rod, the biasing means having a first bias end at least partially receivable in the internal chamber of the ram and a second bias end contactable by the bias face of the collar,
g) wherein the ram supported on the center rod and a surgical tool are relatively manipulatable to move the transverse projection in an axial direction along a second J-slot of the surgical tool and then in both a rotational and axial manner to move the transverse projection into a terminal end of the second J-slot as the engagement finger moves into the second J-slot to thereby block movement of the transverse projection therefrom, and wherein the collar is axially manipulatable along the center rod against the biasing means to align the guide pin with the release slot and then rotatable and axially manipulatable about the center rod to move the guide pin into a locked relationship with the release slot of the center rod with the biasing means providing a biasing force against the ram preventing the engagement finger from releasing from the second J-slot of the surgical tool thereby locked to the connected tool holder, and
h) wherein the collar is rotatably and axially manipulatable to remove the guide pin from the release slot and then the collar is axially manipulatable in a proximal direction along the center rod to relax the biasing means against the ram so that the ram supported on the center rod and the surgical tool are relatively manipulatable to move the engagement finger in an axial manner out of the second J-slot of the surgical tool and then in both a relative rotational and axial manner to thereby move the transverse projection out of the second J-slot to thereby release the surgical tool from the tool holder.

16. The tool holder of claim 15 wherein the release slot is selected from the group consisting of a J-slot, a double J-slot, and a T-slot.

17. A surgical tool holder adapted to connect to a surgical tool, the tool holder comprising:
a) a center rod comprising a linear axis extending from a first, proximal shank end to a second, distal tool end;
b) a tracking groove extending along a surface of the center rod parallel to the linear axis from a first groove end adjacent to the tool end to a second groove end proximal from the tool end, the tracking groove communicating with a first J-slot provided in the surface of the center rod at an intermediate location between the first and second groove ends;
c) a tool interface comprising at least one transverse projection extending radially outwardly in a fixed manner beyond a diameter of the center rod proximate the distal tool end;
d) a ram disposed proximate the distal tool end and comprising a ram bore receiving the center rod in a movable relationship therewith, wherein the ram comprises a first ram end from which at least one engagement finger projects parallel to the linear axis of the center rod, and an internal chamber open to a second ram end, wherein a locking pin supported by the ram projects into the ram bore and is movable along the tracking groove of the center rod;

e) a collar having a collar bore through which the center rod movably passes, the collar having a bias face at a distal collar end, wherein a guide pin supported by the collar projects into the collar bore and is movable along the tracking groove and the first J-slot of the center rod; and f) a biasing means positioned between the collar and the ram in a movable relationship about the center rod, the biasing means having a first bias end at least partially receivable in the internal chamber of the ram and a second bias end contactable by the bias face of the collar, g) wherein the ram supported on the center rod and a surgical tool are relatively manipulatable to move the transverse projection in an axial direction along at least one second J-slot of the surgical tool and then in both a rotational and axial manner to move the transverse projection into a terminal end of the second J-slot as the engagement finger moves into the second J-slot to thereby block movement of the transverse projection therefrom, and wherein the collar is axially manipulatable along the center rod against the biasing means to align the guide pin with the first J-slot and then rotatable and axially manipulatable about the center rod to move the guide pin into a locked relationship with the first J-slot of the center rod with the biasing means providing a biasing force against the ram preventing the engagement finger from releasing from the second J-slot of the surgical tool thereby locked to the connected tool holder, and h) wherein the collar is rotatably and axially manipulatable to remove the guide pin from the first J-slot and then the collar is axially manipulatable in a proximal direction along the center rod to relax the biasing means against, the ram so that the ram supported on the center rod and the surgical tool are relatively manipulatable to move the engagement finger in an axial manner out of the second J-slot of the surgical tool and then in both a relative rotational and axial manner to move the transverse projection out of the second J-slot to thereby release the surgical tool from the tool holder.

18. The tool holder of claim 17 wherein there are two diametrically opposed transverse projections.

19. The tool holder of claim 17 wherein there are two diametrically opposed engagement fingers.

20. A surgical tool holder adapted to connect to a surgical tool, the tool holder comprising:

a) a center rod comprising a linear axis extending from a first, proximal shank end to a second, distal tool end;

b) a tracking groove extending along a surface of the center rod parallel to the linear axis from a first groove end adjacent to the tool end to a second groove end proximal from the tool end, the tracking groove communicating with a release slot provided in the surface of the center rod at an intermediate location between the first and second groove ends;

c) a tool interface comprising at least one transverse projection extending radially outwardly in a fixed manner beyond a diameter of the center rod proximate the distal tool end;

d) a ram disposed proximate the distal tool end and comprising a ram bore receiving the center rod in a movable relationship therewith, wherein the ram comprises a first ram end from which at least one engagement finger projects parallel to the linear axis of the center rod, and an internal chamber open to a second ram end, wherein a locking pin supported by the ram projects into the ram bore and is movable along the tracking groove of the center rod;

e) a collar having a collar bore through which the center rod movably passes, the collar having a bias face at a distal collar end, wherein a guide pin supported by the collar projects into the collar bore and is movable along the tracking groove and the release slot of the center rod; and f) a biasing means positioned between the collar and the ram in a movable relationship about the center rod, the biasing means having a first bias end at least partially receivable in the internal chamber of the ram and a second bias end contactable by the bias face of the collar, g) wherein the ram supported by the center rod and a surgical tool are relatively manipulatable to move the engagement finger and the transverse projection in an axial direction along an interface slot of the surgical tool and then in a rotational manner to cause the transverse projection to bear against a back surface of a support for the surgical tool, and wherein the collar is axially manipulatable along the center rod against the biasing means to align the guide pin with the release slot and then to move the guide pin into a locked relationship with the release slot of the center rod with the biasing means providing a biasing force against the ram preventing the transverse projection from releasing from its engaged relationship with the support of the surgical tool thereby locked to the connected tool holder, and h) wherein the collar is rotatably and axially manipulatable to remove the guide pin from the release slot and then the collar is axially manipulatable in a proximal direction along the center rod to relax the biasing means against the ram so that the ram supported on the center rod and the surgical tool are relatively manipulatable to remove the transverse projection from the support surface of the surgical tool and to move the engagement finger out of the interface slot to thereby release the surgical tool from the tool holder.

21. The tool holder of claim 20 wherein the shank end of the tool driver is adapted to connect to a tool driver.

22. The tool holder of claim 20 wherein the bias face of the collar is receivable into the internal chamber of the ram with the biasing means disposed therebetween.

23. The tool holder of claim 20 wherein the release slot is selected from the group consisting of a J-slot, a double J-slot, and a T-slot.

24. The tool holder of claim 20 wherein a through bore is provided along the linear axis of the center rod.

25. The tool holder of claim 20 wherein the center rod comprises a shoulder adjacent to the distal tool end, the shoulder providing a surface against which a surgical tool contacts when it is locked to the tool holder.

* * * * *

UNITED STATES PATENT AND TRADEMARK OFFICE
CERTIFICATE OF CORRECTION

| | | |
|---|---|---|
| PATENT NO. | : 7,988,692 B2 | Page 1 of 1 |
| APPLICATION NO. | : 11/962562 | |
| DATED | : August 2, 2011 | |
| INVENTOR(S) | : Lechot | |

It is certified that error appears in the above-identified patent and that said Letters Patent is hereby corrected as shown below:

Column 8, Line 43 - e) delete "of"

Signed and Sealed this
Fourth Day of October, 2011

David J. Kappos
*Director of the United States Patent and Trademark Office*